United States Patent [19]

Warren

[11] 4,301,253

[45] Nov. 17, 1981

[54] PROCESS FOR THE SELECTIVE PRODUCTION OF ETHANOL AND METHANOL DIRECTLY FROM SYNTHESIS GAS

[75] Inventor: Barbara K. Warren, Charleston, W. Va.

[73] Assignee: Union Carbide Corporation, New York, N.Y.

[21] Appl. No.: 190,905

[22] Filed: Sep. 25, 1980

[51] Int. Cl.$^3$ .................... C07C 27/06; C07C 31/08
[52] U.S. Cl. .................................. 518/700; 252/437; 252/441; 44/54
[58] Field of Search ........................................ 518/700

[56] References Cited

U.S. PATENT DOCUMENTS

| | | |
|---|---|---|
| 2,490,488 | 12/1949 | Stewart . |
| 2,535,060 | 12/1950 | Gresham . |
| 2,549,470 | 4/1951 | Howk et al. . |
| 2,636,046 | 4/1953 | Gresham . |
| 3,248,432 | 4/1966 | Riley et al. . |
| 3,285,948 | 11/1966 | Butter . |
| 3,387,043 | 6/1968 | Kuraishi et al. . |
| 3,972,952 | 8/1976 | Clark . |
| 4,111,837 | 9/1978 | Taylor . |
| 4,122,110 | 10/1978 | Sugier et al. . |
| 4,133,966 | 1/1979 | Pretzer et al. . |
| 4,162,262 | 7/1979 | Ellgen et al. . |
| 4,168,391 | 9/1979 | Slinkard et al. . |
| 4,170,605 | 10/1979 | Williamson et al. . |
| 4,190,729 | 2/1980 | Forster ........................... 560/232 |

Primary Examiner—Howard T. Mars
Attorney, Agent, or Firm—François M. Fazio

[57] ABSTRACT

Alkanols are selectively produced as the major product directly from synthesis gas under mild conditions using a homogeneous ruthenium catalyst, a halogen or halide promoter and a phosphine oxide compound as solvent.

8 Claims, No Drawings

PROCESS FOR THE SELECTIVE PRODUCTION OF ETHANOL AND METHANOL DIRECTLY FROM SYNTHESIS GAS

BACKGROUND OF THE INVENTION

Within the past decade the price of crude oil, the basis for most petroleum products, has increased significantly; in addition its availability in needed quantities has at times been severely curtailed. This has created many problems to the manufacturers and consumers leading to attempts to reduce reliance on crude oil as the basic starting material. A major product dependent on adequate supplies of crude oil is ethanol, which has been manufactured in significant quantities by the hydration of ethylene derived from petroleum or crude oil. The increased costs of crude oil are, however, making this process less economical at a time when the demand for ethanol for use in fuels, such as gasohol, or as an intermediate for producing other organic compounds, such as ethylene (from dehydration), is increasing at an unpredictable rate. Thus, much effort is being expended to the development of alternate processes for the production of ethanol at economically acceptable costs from other sources.

While the production of ethanol by the well known fermentation process is well established, this process competes with the use of the starting materials generally used, grains and sugars, as foodstuffs. Further, in many instances the feedstocks are not readily available at the plant site and the processes are multi-step procedures requiring provisions for fermentation, distillation and disposal of residual solid wastes. To attempt to supply the anticipated demand for ethanol solely by additional fermentation plants could result in a significant disruption in the amount of feed grain available for human needs. As a result methods which do not severely disrupt these needs are preferred.

Such procedures involve the use of synthesis gas, a mixture of carbon monoxide and hydrogen. This is an alternate feedstock which is inexpensive and increasingly desirable because it can be derived from non-petroleum sources such as coal.

Among the references relating to the production of organic compounds, including ethanol, of particular interest are those using complexes containing cobalt or osmium or ruthenium compounds as a component of the catalyst complex in the reaction of synthesis gas. Basically the known processes involve the catalytic homologation of methanol with synthesis gas at elevated temperatures and pressures, with most processes yielding a mixture of products that are subsequently separated. To our present knowledge there is no single reference that can be said to individually teach how to selectively produce ethanol at commercially significant efficiencies directly from synthesis gas.

The direct, homogeneous conversion of synthesis gas to produce some ethanol is discussed in U.S. Pat. No. 2,534,018 issued to W. F. Gresham on Dec. 12, 1950. In this disclosure a cobalt-based catalyst and high pressures are used.

In U.S. Pat. No. 2,535,060 issued to W. F. Gresham on Dec. 26, 1950, there is described a process for preparing mixtures of monohydric alcohols by the reaction of a mixture of carbon monoxide, hydrogen and a hydroxylated solvent at a temperature of from 150° C. to 300° C. and a pressure of from 200 to 1,000 atmospheres using a ruthenium-containing catalyst and an alkaline reagent to control pH within the range of 7 to 11.5. The reference clearly states that it is essential that the reaction take place in the liquid phase and that water and any alcohol can be used as the liquid reaction medium; it also mentions that experimental evidence indicates that the liquid reaction medium may participate in the reaction. The chief products obtained are hydroxyalkanes having from 2 to 10 carbon atoms but there does not seem to be any indication of selectivity to any one specific alkanol.

A closely related reference is U.S. Pat. No. 2,549,470 issued to B. W. Howk et al on Apr. 17, 1951, which claims a process for selectively producing straight chain alkanols having from 3 to 50 carbon atoms by the liquid phase reaction of a mixture of carbon monoxide, hydrogen and a hydroxylated solvent at a temperature of from 100° C. to 250° C. and a pressure of from 200 to 1,000 atmospheres using a ruthenium-containing catalyst. These examples do show the production of small amounts of methanol and ethanol but the process essentially selectively produces the higher alkanols.

In U.S. Pat. No. 2,636,046 issued to W. F. Gresham on Apr. 21, 1953 there is discussed a direct, homogeneous process for producing ethanol from synthesis gas at low selectivities using cobalt-based catalysts and high pressures.

A cobalt-based catalyst is used in U.S. Pat. No. 3,248,432 issued to A. D. Riley et al on Apr. 26, 1966, to produce ethanol. In this reference methanol is reacted with carbon monoxide and hydrogen at a pressure in excess of 3,000 to 4,000 psi and a temperature of from about 150° C. to 250° C. in the presence of a modified catalyst complex containing cobalt, an iodine promoter and a phosphorus compound as defined. In essence this is an homologation process using a cobalt-based catalyst.

Another homologation process is disclosed in U.S. Pat. No. 3,285,948 issued to C. N. Butter et al on Nov. 15, 1966. This patent discloses the use of halides of ruthenium and osmium as second promoters in conjunction with cobalt and iodine for the production of ethanol by the homologation reaction of methanol with carbon monoxide and hydrogen.

The invention claimed in U.S. Pat. No. 3,387,043 issued to M. Kuraishi et al on June 4, 1968 is the improvement of adding water to the homologation reaction of ethanol, n-propanol or n-butanol with carbon monoxide and hydrogen using a catalyst containing cobalt and iodine.

The heterogeneous reaction of synthesis gas to produce ethanol at selectivities of less than 40 mole percent is discussed in U.S. Pat. No. 2,490,488 issued to S. G. Stewart on Dec. 6, 1949. In this patent the catalyst was molybdenum disulfide and an alkaline compound of an alkali metal.

A solid, heterogeneous catalyst is used in the homologation reaction disclosed in U.S. Pat. No. 3,972,952 issued to R. T. Clark on Aug. 3, 1976. The catalytic agent is a base promoter such as an oxide, hydroxide or salt of the alkali and alkaline earth metals and a metal of the group ruthenium, rhodium, palladium, osmium, iridium and platinum on an inert solid support material comprising alumina. In this process an alkanol is converted to a higher alkanol.

In U.S. Pat. No. 4,111,837 issued to P. D. Taylor on Sept. 5, 1978, methanol is reacted in liquid phase with carbon monoxide and hydrogen at a temperature of from 100° C. to 350° C. and a pressure of from 1,000 to 15,000 psi in the presence of a heterogeneous catalyst containing a cobalt derivative and a methanol-insoluble rhenium derivative.

Another heterogeneous reaction using a mixture of four essential elements (1) copper, (2) cobalt, (3) chromium, iron, vanadium or maganese, and (4) an alkali metal in the catalyst to convert synthesis gas to ethanol is described in U.S. Pat. No. 4,122,110 issued to A. Sugier et al on Oct. 24, 1978. In this process the selectivity is below 40 weight percent.

The homologation of methanol with carbon monoxide and hydrogen to produce ethanol is described in U.S. Pat. No. 4,133,966 issued to W. R. Pretzer et al on Jan. 9, 1979. In the process disclosed the catalyst system is cobalt acetylacetonate a tertiary organo Group VA—compound, an iodine compound as a first promoter and ruthenium compound as a second promoter. While the reaction is said to be selective to the production of ethanol, the experimental data fails to show any selectivity values greater than 60 mole percent.

The use of rhodium in combination with thorium and/or uranium to produce two-carbon atom oxygenated products from synthesis gas using a heterogeneous catalyst is disclosed in U.S. Pat. No. 4,162,262 issued to P. C. Ellgen et al on July 24, 1979. This patent stresses the minimization of methanol coproduction.

The homologation of methanol with synthesis gas in the liquid phase using a cobalt carbonyl catalyst is disclosed in U.S. Pat. No. 4,168,391 issued to W. E. Slinkard et al on Sept. 18, 1979. The improvement claimed in this patent is the use of a non-polar, substantially inert, oxygenated hydrocarbon solven that does not coordinate strongly with cobalt carbonyl as the solvent during the reaction.

A ruthenium based catalyst is disclosed in U.S. Pat. No. 4,170,605 issued to R. C. Williamson et al on Oct. 9, 1979; however, the process is one which selectively produces ethylene glycol, not alkanols.

Homologation is also disclosed in U.S. Pat. No. 4,190,729 issued to D. Foster on Feb. 26, 1980, in which a tertiary phosphine oxide is used as a stabilizer during the homologation reaction of methanol to ethanol, acetaldehyde and methyl acetate employing a cobalt-based catalyst.

The selective production of ethanol by the homologation of methanol with carbon monoxide and hydrogen under selected ratios and reaction conditions catalyzed by cobalt, ruthenium, an iodine promoter, and a phosphine ligand is shown in commonly assigned patent application Ser. No. 91,241, filed on Nov. 15, 1979 by R. A. Fiato.

In another commonly assigned patent application, Ser. No. 91,242, filed on Nov. 15, 1979 by B. D. Dombek, there is disclosed a process for selectively converting synthesis gas to ethylene glycol, ethanol and methanol using a homogeneous ruthenium carbonyl complex as the catalyst and a solvent which has a dielectric constant of at least 2 determined at 25° C. or at its melting point, whichever is higher; the process also contemplates the use of a Lewis base promoter.

As is evident from the above, there is little existing prior art concerned with the direct selective production of ethanol from synthesis gas. In most instances ethanol is produced by homologation reactions, not directly, and in those instances in which a direct process is disclosed the process was not a homogeneous process or the ethanol selectivities and efficiencies achieved are not commercially acceptable.

SUMMARY OF THE INVENTION

It has now been found that ethanol can be produced selectively as the major product directly from synthesis gas under mild conditions using a homogeneous catalyst. The catalyst system contains a ruthenium compound, an halogen or halide promoter (preferably based on iodine or bromine) and a phosphine oxide compound as solvent. One can also include other promoters, if desired.

DESCRIPTION OF THE INVENTION

In the catalytic reactions of synthesis gas to produce organic compounds, there are basically three significant parameters or criteria by which the catalysts are judged; namely, stability, activity and selectivity. Stability relates to how long the catalyst remains functional before either breaking down or losing catalytic effect; activity relates to the amount of reactants the catalysts converts per unit of time; selectivity relates to the quantity of desired product produced, as compared to undesired compounds, during the catalytic reaction. The ideal situation is to have high values for all of these parameters, but this ideal is seldom, if ever, achieved. In fact, experience has shown that an improvement in one of the parameters often tends to have a detrimental effect on one or both of the other parameters and the ultimate result is usually an overall less efficient process.

The present invention is directed to a catalytic process in which the three basic parameters are maximized to a significant degree and in which ethanol is directly and selectively produced in a homogeneous process, and to the catalyst compositions used in such process. In the process of this invention ethanol is obtained as the major product directly from synthesis gas under mild conditions using a homogeneous ruthenium catalyst. Methanol, propanol, ethylene glycol and methane are the significant by-products, all of which can be separated and recovered, or recycled, if desired. Alternately, the mixture of products could be used with a minimum of separation as a fuel.

Best results are achieved in the process of this invention, leading to high selectivities and rates to ethanol and the above mentioned alkanols, when using a ruthenium catalyst, a halide or halogen promoter and a phosphine oxide compound as the solvent. The advantages observed by the instant process in the production of ethanol, as compared to other known processes, include the fact that it is a homogeneous process, it uses synthesis gas as a feedstock rather than petroleum based feedstocks, it produces a major amount of ethanol directly in a single step, the selectivity to ethanol is unexpectedly high and the selectivity to ethanol plus methanol (which can be recycles to retard further formation of methanol) is even higher, the reaction can be conducted at what are considered mild conditions by those skilled in this art, and the number of significant by-products produced are few, but useful. The method has significant economic and process advantages due to the fact that since it is a homogeneous reaction there is greater efficiency in removing heat of reaction and thus a corresponding ease of heat control; further, there is greater ease in characterizing the catalytic and related species present in the reaction, which helps in controlling the process, analyzing the process and products, and optimizing the final results.

The invention is advantageous when compared to other known processes when the intent is to produce a mixture of compounds, e.g. alkanols, for fuel use in that it is a one-step, homogeneous, direct process from synthesis gas to yield a mixture high in alcohols that can be used with a minimum of purification. Thus the use of this invention for the manufacture of compositions useful as fuels is of significant importance in today's economy.

The ruthenium component of the catalyst can be supplied from any number of sources and those skilled in the art are fully familiar with the many classes of ruthenium compounds that can be used to supply the ruthenium component. Thus, any of the ruthenium compounds such as the ruthenium salts, oxides, carbonyls, organic carboxylic acid salts, or ruthenium metal itself, which may form soluble ruthenium carbonyl or hydrocarbonyl compounds under the reaction conditions can be used. The ruthenium complexes which catalyze the reaction are not specifically known; they can be monoruthenium or polyruthenium complexes. Among the ruthenium compounds that can be used as the source for the ruthenium component one can mention ruthenium dioxide, ruthenium sesquioxide, ruthenium tetraoxide, ruthenium trichloride or tribromide or triiodide, ruthenium acetate, ruthenium acetylacetonate, ruthenium propionate, ruthenium octanoate, ruthenium pentacarbonyl, triruthenium dodecacarbonyl, ruthenium carbonyl hydride, diruthenium nonacarbonyl, ruthenium (2,4-pentanedionate), or any other ruthenium compound which can generate a soluble ruthenium complex under the reaction conditions. They can be used individually or as mixtures of two or more ruthenium compounds.

The concentration of ruthenium compound charged to the reaction can be from 0.01 to 30 weight percent of the total weight of the reaction mixture, based on contained ruthenium, it is preferably from 0.2 to 10 weight percent and most preferably from 0.5 to 5 weight percent.

The preferred promoters are those halogen containing compounds capable of generating HI or HBr during the reaction, including elemental iodine and bromine, i.e., HI or HBr precursors. Some stable halide salts, e.g. KI, CsI, were also found to be good promoters to selectively produce mixtures of ethanol plus methanol, and under certain conditions produce ethanol as the major product. Illustrative of suitable halogen promoters, or HI or HBr precursors, one can mention iodine, bromine, potassium iodide, tetramethylammonium iodide, trimethylsulfonium iodide, methyl iodide, butyl iodide, tetrabutylammonium iodide, hydrogen iodide, tetramethylphosphonium iodide, cesium iodide, tetraethylammonium iodide, cobalt iodide, as well as the corresponding bromide compounds. Any source of iodine or bromine capable of generating HI or HBr in situ can be used; these are well known to those of average skill in this art. Also among the useful compounds are the alkyl iodides and bromides having from 1 to about 10 carbon atoms, as well as any other organic iodine or bromine compound capable of producing HI or HBr in situ. Further, one can use mixtures of the elemental halogens and/or the halogen compounds. As used in this application the term "halogen promoter" includes the elemental forms of iodine and bromine as well as the compounds containing these elements.

The amount of halogen promoter charged to the reaction will vary from an amount sufficient to produce an HI and/or HBr/Ru atom mole ratio of 0.001:1 to 5:1, preferably from 0.01:1 to 3:1, most preferably from 0.1:1 to 2:1, in situ during the reaction. It has been observed, however, that at ratios above about 3:1 the reaction will not proceed at a substantial rate even though it will selectively produce alkanols in major amounts. Care must be exercised in selection of a particular promoter compound. Thus, it was found that when the organic quarternary halide salts were used as promoters, even at high promoter to ruthenium levels (greater than 3:1) the reaction proceeded well at low temperatures, e.g. below about 210° C., but at higher temperatures, e.g. above about 240° C., decomposition of such promoters to generate the hydrogen halide proceeds to such a degree that the hydrogen halide to ruthenium ratio becomes greater than 3:1 and the reaction will not proceed as well.

The preferred halogen promoters can also be supplemented, if desired, by the inclusion of other promoters that are known in the art. Thus, it has been found that the inclusion of selected promoters, in amounts known to those skilled in the art, such as the Lewis bases (e.g. $R_3N$, $R_3P$, $R_2S$ type compounds and zinc iodide) did not harm the reaction and in certain instances were beneficial.

It was also noted that promoter combinations containing an alkali metal halide as one of the components of the combination were effective and that when used in metal halide to ruthenium atom ratios of about less than 1:1 served to promote the rate at which ethanol was selectively produced. At high levels of alkali metal halide to ruthenium atom, methanol and ethanol are produced at a faster rate but methanol may be the major product. In addition it was observed that the use of an alkali metal halide as the sole promoter at a ratio to ruthenium greater than 2:1 and as high as 20:1 results in good rates to mixtures of ethanol plus methanol but that ethanol was produced at a lower selectivity than when the alkali metal halide to ruthenium ratio was less than 2:1.

Also present in the reaction is an organic phosphine oxide compound as solvent, which can be represented by the general formula:

$$R'_3P=O$$

in which R' is an organic radical such as an unsubstituted or substituted alkyl group having from 1 to 20 carbon atoms, preferably 1 to 8 carbon atoms or an unsubstituted or substituted aryl group having from 6 to 10 ring carbon atoms. The alkyl or aryl groups can be substituted with oxygen, sulfur, phosphorus or nitrogen containing groups which do not unduly interfere with the reaction. These compounds are well known to those skilled in the art and illustrative thereof one can mention tripropylphosphine oxide, di(2-methoxyethoxymethyl) methylphosphine oxide, triphenylphosphine oxide, trioctylphosphine oxide, di-n-n-propyl-n-butylphosphine oxide, triallylphosphine oxide, tricyclohexylphosphine oxide, and the like. The phosphine oxides can be used alone or in combination with other solvents known to be useful to those skilled in the art.

The amount of phosphine oxide used can be from 1 to 100 weight percent; preferably from 10 to 100, of the total weight of solvent charged to the reactor with the balance being a conventional solvent known to those skilled in the art, e.g. 1,4,7,10,13,16-hexaoxacyclooctadecane, diphenyl ether, sulfolane, N-methylpyrrollidone, tetraglyme, and the like.

The reaction is carried out at a temperature of from about 100° C. to 350° C., preferably from 160° C. to 280° C. The preferred range is more satisfactory with the onium salts in order to obtain better control of the hydrogen halide to ruthenium ratio.

The reaction can be carried out at total pressures of from 500 psi to 20,000 psi or more; preferably from 1,000 psi to 12,500 psi; and most preferably from 2,500 psi to 8,000 psi. Variations in pressure can affect the rate and selectivity to ethanol and those skilled in the art can readily ascertain the best conditions to employ with each particular catalyst, promoter and solvent system employed by routine procedures. While higher pressures tend to result in greater productivities, they may not be justified economically since they require higher capital investment and since, generally, good rates can be achieved at the lower pressures indicated.

The ratio of carbon monoxide to hydrogen ($CO:H_2$) in the synthesis gas feed mixture can range from 0.1:1 to 10:1; preferably from 0.25:1 to 4:1; and most preferably from 0.33:1 to 2:1.

The improved process and catalyst of this invention result in the selective production of ethanol or mixtures containing ethanol directly from synthesis gas at significantly better yields than heretofore achieved. By use of this invention ethanol or synthetic fuel mixtures can be produced directly under what are technically considered relatively mild reaction conditions using a homogeneous catalyst system. The results achieved and the advantages noted were completely unexpected and unpredictable from the published knowledge.

In the examples the product yields are reported in values of weight of product produced, the rates are reported in moles/liter/hour and the selectivity in weight percent, unless otherwise indicated. Carbon dioxide produced by the water gas shift reaction is ignored in the selectivity calculations. Standard analytical procedures were used to analyze for gaseous and liquid components present in the final reaction product.

Three standard procedures were used for the reactions described in the examples.

Standard Procedure A

Triruthenium dodecacarbonyl, promoter and 75 ml of tripropylphosphine oxide were placed in a back-mixed autoclave having a net volume of 128 ml and heated, with stirring, to 55° C. The reactor was pressured to 500 psi with CO, heated to the desired temperature and pressurized with a $H_2/CO$ mixture (having the desired ratio of $H_2:CO$) to the total desired pressure plus 250 psi. As the reaction proceeded the pressure was allowed to drop 500 psi and then repressured to the original total pressure with the synthesis gas. After a total of 2,000 psi of synthesis gas had reacted, or two hours had passed, whichever occurred first, the reactor was rapidly cooled to 40° C. The gaseous components in the reactor were vented to and collected in a 3 liter stainless steel bomb and vapor phase chromatographic analyses were performed to determine hydrogen, carbon monoxide, carbon dioxide and $C_1$ to $C_4$ carbon, hydrogen and oxygen containing gaseous organic compounds. The liquid components in the reactor were weighed and analyzed by vapor phase chromatograph and other conventional analytical methods to ascertain their identity and concentration.

Standard Procedure B

Triruthenium dodecacarbonyl, promoter and 50 ml of tripropylphosphine oxide were placed in a glass lined rocker autoclave having a net volume of 500 ml and pressurized with a $H_2/CO$ mixture (having the desired ratio) to a pressure such that after the desired temperature has been attained, the pressure in the autoclave was at 4,600 psi to 5,000 psi. The autoclave was repressurized with synthesis gas when the pressure had dropped to about 4,000 psi. Two hours after the initial attainment of the desired temperature, the autoclave and its contents were cooled to 0° to 40° C., gaseous components vented to the atmosphere and the liquid components were weighed and analyzed by vapor phase chromatograph methods using at least two different columns. The total pressure is reported as the average pressure for the run.

Standard Procedure C

This procedure is identical to Standard Procedure A except that the reaction proceeded until 6,000 psi of synthesis gas had reacted or four hours had passed, whichever occurred first, and that the gaseous components were vented and not analyzed; therefore, selectivities reported are based on the weight percent of liquid products analyzed by the vapor phase chromatographic methods.

The following examples serve to further illustrate the invention.

EXAMPLE 1

Ethanol was selectively produced using Standard Procedure A. In this experiment 16 mgram atoms of Ru, as triruthenium dodecacarbonyl, 5.6 mmoles of elemental iodine and 75 ml of tripropylphosphine oxide were used; the $H_2/CO$ ratio was 2:1 and the reaction was carried out at a total pressure of 6,000 psi at 240° C. There were produced as determined by vapor phase chromatograph analysis, 2.12 g of ethanol, 1.03 g of methanol, 0.12 g of propanol, 0.82 g of methane and 0.17 g of other liquid products; slight traces of gaseous or other liquid products were also detected. Ethanol was produced at the rate of 2.05 moles/liter/hour at a selectivity of 50 weight percent; the selectivity to ethanol plus methanol was 74 weight percent. The results show that ethanol or mixtures of alkanols can be produced at high selectivity directly from synthesis gas by this invention.

EXAMPLE 2

Standard Procedure A was again employed using 8 mgram atoms of Ru, as ruthenium dodecacarbonyl, 4 mmoles of elemental iodine and 75 ml of tripropylphosphine oxide; the $H_2/CO$ ratio was 2:1. The reaction was carried out at a total pressure of 6,000 psi at 240° C. There were produced 2.46 g of ethanol, 0.97 g of methanol, 0.19 g of propanol, 0.95 grams of methane and 0.18 g of other liquid products; slight traces of gaseous or other liquid products were also detected. Ethanol was produced at a rate of 1.9 moles/liter/hour at a selectivity of 52 weight percent; the selectivity to ethanol plus methanol was 72 weight percent; illustrating the ability to directly produce alkanols at high selectivity from synthesis gas.

EXAMPLE 3

Standard Procedure A was employed using 24 mgram atoms of Ru, as ruthenium dodecacarbonyl, 15.6 mmoles of elemental iodine and 75 ml of tripropylphosphine oxide; the $H_2/CO$ ratio was 1:1. The reaction was carried out at a total pressure of 6,000 psi at 195° C. There were produced 2.48 g of ethanol, 1.03 g of methanol, 0.1 g of propanol, 0.62 g of methane and 0.27 g of other liquid products; slight traces of gaseous or other liquid products were also detected. Ethanol was produced at the rate of 0.6 mole/liter/hour at a selectivity to ethanol plus methanol of 78 weight percent. The results show that at lower temperatures high selectivity to alkanols is still achieved though at a lower rate.

EXAMPLES 4 to 23

Standard Procedure A was followed in these examples in which ethanol and mixtures of ethanol with other alkanols were selectively produced directly from synthesis gas. The reaction conditions and results are summarized in Table I. In the table the partial pressures of $H_2$ and CO present in the synthesis gas mixture charged are recorded, from which the total pressure is readily ascertained. Elemental iodine was used as promoter and the ratio stated is the I/Ru ratio, not the $I_2$/Ru ratio. Selectivity (Sel.) values reported are the area percent ethanol divided by the total area for all vapor phase chromatograph peaks other than water, air and solvent.

EXAMPLES 24 to 76

Table II shows the selective production of ethanol or ethanol plus methanol mixtures directly from synthesis gas by the process of this invention. It illustrates the use of different promoters and solvents as well as variations in the temperature and pressure reaction conditions employable. Unless otherwise indicated all of the examples used 75 ml of tripropylphosphine oxide ($Pr_3PO$), 9 mgram atoms of Ru as triruthenium dodecacarbonyl and a $H_2$/CO ratio of 1:1, and were run at 210° C. Selectivities were determined by vapor phase chromatographic analysis of the liquid products produced and are reported in weight percent.

The procedure used in Examples 55, 56 and 70 through 76 was identical to Standard Procedure A except that the reaction proceeded until 6,000 psi of synthesis gas had reacted or two hours had passed, whichever occurred first.

In all 76 examples the designation moles/liter/hour, indicating the formation rates of products, is based on the reaction solution in the reactor or moles/liter of solution/hour.

TABLE I

| Ex. No. | T °C. | p($H_2$) psi (*) | p(CO) psi (*) | Ru mg-atoms | I/Ru | Formation Rates moles/liter/hour | | | | Total mols of gas taken up | Time, hr. | Sel. |
|---|---|---|---|---|---|---|---|---|---|---|---|---|
| | | | | | | ETOH | MeOH | $CH_4$ | $CO_2$ | | | |
| 4 | 240 | 2000 | 2000 | 8 | 1.0 | .325 | .096 | 3.570 | 4.517 | .317 | .183 | 62.55 |
| 5 | 225 | 2500 | 2500 | 12 | .4 | .722 | .472 | .497 | .773 | .326 | .966 | 61.66 |
| 6 | 195 | 3000 | 3000 | 24 | 1.3 | .571 | .348 | .411 | .664 | .347 | 1.266 | 65.18 |
| 7 | 225 | 3750 | 2250 | 8 | 0.7 | 1.13 | 1.17 | 1.73 | 1.63 | .326 | .40 | 50.68 |
| 8 | 210 | 2500 | 1500 | 24 | 0.4 | .288 | .194 | 0.619 | 0.597 | .336 | 1.25 | 63.66 |
| 9 | 195 | 3125 | 1875 | 16 | 1.0 | .345 | .210 | 0.524 | 0.498 | .347 | 1.5 | 64.83 |
| 10 | 240 | 4200 | 1800 | 16 | 0.4 | 2.06 | 1.81 | 2.07 | 1.926 | .3165 | .18 | 47.34 |
| 11 | 225 | 2100 | 900 | 24 | 1.0 | .150 | .001 | 0.625 | 0.717 | .326 | 1.58 | 50.71 |
| 12 | 210 | 3500 | 1500 | 8 | 1.3 | .408 | .233 | 0.561 | 0.551 | .336 | 1.33 | 66.10 |
| 13 | 195 | 2800 | 1200 | 12 | 0.7 | .197 | .144 | 0.22 | 0.193 | .260 | 2. | 59.67 |
| 14 | 240 | 3750 | 1250 | 24 | 0.7 | 1.16 | 1.23 | 4.40 | 2.80 | .3165 | 0.2 | 52.98 |
| 15 | 225 | 3000 | 1000 | 16 | 1.3 | .397 | .234 | 1.55 | 1.18 | .326 | 0.567 | 61.29 |
| 16 | 210 | 4500 | 1500 | 12 | 1.0 | .754 | .623 | 0.920 | 0.920 | .336 | .667 | 57.85 |
| 17 | 195 | 2250 | 250 | 8 | 0.4 | .078 | .102 | 0.067 | 0.087 | .130 | 2.0 | 48.72 |
| 18 | 240 | 4000 | 2000 | 16 | .4 | 1.626 | 1.578 | 1.467 | 1.156 | .317 | .3 | 54.81 |
| 19 | 240 | 4000 | 2000 | 16 | .7 | 2.053 | 1.439 | 2.267 | 1.911 | .317 | .3 | 61.62 |
| 20 | 240 | 4000 | 2000 | 16 | 1.0 | 1.699 | 1.03 | 2.715 | 2.228 | .317 | .383 | 63.21 |
| 21 | 240 | 4000 | 2000 | 8 | 1 | 1.86 | 1.08 | 2.186 | 1.858 | .317 | .366 | 64.16 |
| 22 | 240 | 4000 | 2000 | 24 | 1 | 1.899 | 1.452 | 5.013 | 3.409 | .317 | .266 | 56.45 |
| 23 | 210 | 4000 | 2000 | 8 | 1 | .704 | .433 | .285 | .393 | .336 | .983 | 64.54 |

*Initial pressure; as the reaction progressed it was recharged at the original $H_2$:CO ratio; average pressure was the total pressure with the range varying ± 250 psi.

TABLE II

| Ex. | Total P PSI | Promoter (mmoles) | Formation Rates Moles/L/Hr. | | Selectivities | | Standard Procedure |
|---|---|---|---|---|---|---|---|
| | | | MeOH | EtOH | EtOH Wt. % | EtOH+ MeOH Wt. % | |
| 24 | 12,500 | $Me_rNI$(18) | 3.04 | 2.56 | 44.9 | 82.6 | C |
| 25 | 12,500 | KI (4) | 1.20 | 2.25 | 63.4 | 90.4 | C |
| 26 | 6,000 | $I_2$(2) | .11 | .37 | 68.7 | 84.3 | C |
| 27 | 6,000 | $I_2$(3) | .07 | .32 | 67.3 | 79.0 | C |
| 28 | 6,000 | KI (18) | .46 | .56 | 52.9 | 84.9 | C |
| 29 | 6,000 | $I_2$(4) | .28 | .59 | 57.1 | 76.8 | C |
| 30 | 4,300$^r$ | $Me_4NI$(18) | .55 | .76 | 63.5 | 91.8 | B |
| 31 | 4,300$^r$ | $Me_3SI$(9) | .16 | .52 | 72.1 | 87.3 | B |
| 32 | 4,300$^r$ | KI (9) MeI (3) | .94 | .83 | 52.2 | 94.2 | B |
| 33 | 4,300$^r$ | MeI (9) | .17 | .49 | 71.3 | 87.5 | B |
| 34 | 4,300$^r$ | MeI (3) | .26 | .62 | — | — | B |
| 35 | 4,300$^r$ | KI (9) BuI (3) | .86 | .76 | 52.8 | 93.9 | B |
| 36 | 4,300$^r$ | KI (18) $I_2$ (3) | 1.12 | .68 | 44.5 | 96.4 | B |
| 37 | 12,500$^b$ | $Bu_4NI$ (18) | .17 | .74 | 51 | 60.3 | C |
| 38 | 6,000 | $I_2$ (6) | .08 | .38 | — | — | C |

TABLE II-continued

| Ex. | Total P PSI | Promoter (mmoles) | Formation Rates Moles/L/Hr. MeOH | Formation Rates Moles/L/Hr. EtOH | Selectivities EtOH Wt. % | Selectivities EtOH+ MeOH Wt. % | Standard Procedure |
|---|---|---|---|---|---|---|---|
| 39 | 6,000 | $I_2$ (1) | .11 | .27 | — | — | C |
| 40 | 6,000 | $I_2$ (9) | .04 | .18 | — | — | C |
| 41 | 12,500[q] | KI (18) HI (4) | 2.55 | 2.25 | — | — | C |
| 42 | 12,500[q] | KI (18) HI (6) | 1.72 | 2.26 | — | — | C |
| 43 | 12,500[q] | KI (18) HI (12) | .47 | 1.53 | — | — | C |
| 44 | 12,500[q,e] | KI (18) HI (2) | 2.91 | 1.71 | — | — | C |
| 45 | 4,300[r] | $Me_4Br$(18) | .44 | .57 | — | — | B |
| 46 | 6,000[d] | $Me_4PI$(36) | .40 | .39 | — | — | C |
| 47 | 4,300[e,p] | $Me_4PCl$(9) | .07 | .02 | — | — | B |
| 48 | 4,300[e,p] | KI(9) | .99 | .43 | — | — | B |
| 49 | 12,500[b,e] | CsI(18) | 1.5 | .32 | — | — | C |
| 50 | 12,500[b,e] | KI(18) | 2.1 | .32 | — | — | C |
| 51 | 12,500[b,e,f] | $Bu_4NI$(18) | .45 | .12 | — | — | C |
| 52 | 12,500[b,e,g,p] | $Bu_4NI$(18) | .43 | .18 | — | — | C |
| 53 | 6,000 | $I_2$(4.5) KI(18) $Bu_3P$(3) | .15 | .34 | — | — | C |
| 54 | 6,000 | $I_2$(4.5) | .22 | .36 | — | — | C |
| 55 | 12,500[b] | $Bu_4NI$(6) MeI (1) | .52 | 1.04 | — | — | C |
| 56 | 12,500[b] | $Bu_4NI$(6) MeI (1) $Bu_3N$(1.5) | .75 | 1.3 | — | — | C |
| 57 | 12,500[b] | KI(18) MeI(3) | .96 | 1.04 | — | — | C |
| 58 | 12,500[b] | KI(18) MeI(3) $Bu_3N$(4) | 1.7 | .81 | — | — | C |
| 59 | 6,000 | $I_2$(4) | .09 | .36 | — | — | C |
| 60 | 6,000 | $I_2$(4) $Bu_4N$(6) | .28 | .59 | — | — | |
| 61 | 6,000 | $I_2$(4) $Bu_3N$(8) | .19 | .41 | — | — | C |
| 62 | 6,000 | $I_2$(4) $Bu_3N$(12) | .27 | .40 | — | — | C |
| 63 | 6,000 | $I_2$(4) $Bu_3N$(18) | .3 | .40 | — | — | C |
| 64 | 4,300 | $Bu_4NI$(6) | .4 | .59 | — | — | B |
| 65 | 4,300 | $Bu_4NI$(6) MeI(35.2) | .009 | .002 | — | — | B |
| 66 | 12,500[b] | $ZnI_2$(1.5) | .71 | 1.25 | — | — | C |
| 67 | 6,000[i,j,m] | $I_2$(4) | .98 | 1.64 | — | — | A |
| 68 | 6,000[i,g,j,m] | $I_2$(4) | .02 | — | — | — | A |
| 69 | 6,000[i,k,m] | $I_2$(4) | .60 | .72 | — | — | A |
| 70 | 6,000[i,j,l,m] | $I_2$(4) | 1.04 | .93 | — | — | A |
| 71 | 6,000[i,j,m] | CsI(4) | .99 | .73 | — | — | A |
| 72 | 6,000[i,j,m] | CsI(2) | .41 | .47 | — | — | A |
| 73 | 6,000[i,j,m] | CsI(8) | .93 | .58 | — | — | A |
| 74 | 6,000[m,n,o] | CsI(6.4) | .21 | .47 | — | — | A |
| 75 | 6,000[m,n,o] | CsI(3.2) | .26 | .43 | — | — | A |
| 76 | 6,000[i,j,m] | KI(4) | 1.0 | .90 | — | — | A |

[b] 3 mgram-atoms Ru as $Ru_3(CO)_{12}$
[d] 18 mgram-atoms Ru as $Ru_3(CO)_{12}$
[e] Some of these examples are for comparative purposes. They do not represent preferred conditions of this invention.
[f] 75 ml of 18-Crown-6 as solvent
[g] 75 ml of sulfolane as solvent
[i] 8 mgram-atoms Ru as $Ru_3(CO)_{12}$
[j] $H_2/CO = 2$
[k] 37.5 ml of $Pr_3PO$ and 37.5 ml 18-C-6 as solvent
[l] 37.5 ml of $Pr_3PO$ and 37.5 ml of sulfolane as solvent
[m] Run at 240° C.
[n] $H_2/CO = 2.33$
[o] 16 mgram-atoms Ru as $Ru_3(CO)_{12}$
[p] Run at 230° C.
[q] 6 mgram-atoms Ru as $Ru_3(CO)_{12}$
[r] 50 ml $Pr_3PO$ as solvent

What is claimed is:

1. A process for the selective, direct production of ethanol or mixtures thereof with other alkanols containing up to three carbon atoms, which method comprises the reaction of carbon monoxide and hydrogen in contact with a homogeneous ruthenium catalyst, a halogen or halide promoter and an organic phosphine oxide compound, wherein said process is carried out at:
    (a) a total pressure of from 500 to 20,000 psi,
    (b) a temperature of from 100° C. to 350° C., (c) the carbon monoxide to hydrogen ratio of the gas mixture charged is from 0.1:1 to 10:1, (d) the ruthenium compound charged is capable of generating a soluble ruthenium complex under the reaction conditions and it is charged at a concentration of from 0.01 to 30 weight percent based on the total weight of the reaction mixture, (e) said promoter is (i) elemental iodine or bromine or a compound thereof which is or is capable of generating hydrogen iodide or hydrogen bromide during the reaction and is charged at an amount sufficient to generate a hydrogen halide to ruthenium atom mole ratio of from 0.001:1 to 5:1 in the reaction mixture, or (ii) an alkali metal halide at a ratio to ruthenium atom as high as 20:1, or (iii) a mixture thereof (f) said organic phosphine oxide is charged at a concentration of from 1 to 100 weight percent of total solvent charged to the reactor.

2. A process as claimed in claim 1 wherein the pressure is from 1,000 to 12,500 psi, the temperature is from 160° C. to 280° C., the carbon monoxide to hydrogen ratio is from 0.25:1 to 4:1, the concentration of ruthenium compound charged is from 0.2 to 10 weight percent, said component (e) promoter which is or is capable of generating hydrogen iodide or hydrogen bromide is present at a halide to ruthenium atom mole ratio of from 0.01:1 to 3:1, the organic phosphine oxide is a trialkylphosphine oxide having from 1 to 20 carbon atoms in each alkyl group and it is charged at a concentration of from 1 to 100 weight percent of the total weight of solvent charged to the reactor.

3. A process as claimed in claim 2 wherein the pressure is from 2,500 to 8,000 psi, the carbon monoxide to hydrogen ratio is from 2:1 to 0.33:1 the concentration of ruthenium compound charged is from 0.5 to 5 weight percent, said component (e) promoter which is or is capable of generating hydrogen iodide or hydrogen bromide is present at a halide to ruthenium atom mole ratio is from 0.1:1 to 2:1.

4. A process as claimed in claim 3 wherein said ruthenium compound is triruthenium dodecacarbonyl.

5. A process as claimed in claim 3 wherein the halogen promoter initially charged is elemental iodine.

6. A process as claimed in claim 3 wherein the halogen promoter initially charged is hydrogen iodide.

7. A process as claimed in claim 1 wherein said organic phosphine oxide is charged at a concentration of from 20 to 100 weight percent.

8. A process as claimed in claim 1 wherein methanol is recycled to the reaction mixture.

* * * * *